US011939285B2

(12) United States Patent
Tung

(10) Patent No.: US 11,939,285 B2
(45) Date of Patent: Mar. 26, 2024

(54) 4-HYDROXYBUTYRIC ACID ANALOGS

(71) Applicant: Concert Pharmaceuticals, Inc., Lexington, MA (US)

(72) Inventor: Roger D. Tung, Lexington, MA (US)

(73) Assignee: SUN PHARMACEUTICAL INDUSTRIES, INC., Princeton, NJ (US)

( * ) Notice: Subject to any disclaimer, the term of this patent is extended or adjusted under 35 U.S.C. 154(b) by 38 days.

(21) Appl. No.: 17/514,416

(22) Filed: Oct. 29, 2021

(65) Prior Publication Data

US 2022/0162146 A1    May 26, 2022

Related U.S. Application Data

(63) Continuation of application No. 16/739,422, filed on Jan. 10, 2020, now Pat. No. 11,161,798, which is a continuation of application No. 15/810,526, filed on Nov. 13, 2017, now Pat. No. 10,532,971, which is a continuation of application No. 14/732,859, filed on Jun. 8, 2015, now Pat. No. 9,815,763, which is a continuation of application No. 13/914,127, filed on Jun. 10, 2013, now Pat. No. 9,051,261, which is a continuation of application No. 13/265,609, filed as application No. PCT/US2010/031981 on Apr. 22, 2010, now Pat. No. 8,461,197.

(60) Provisional application No. 61/287,561, filed on Dec. 17, 2009, provisional application No. 61/214,382, filed on Apr. 23, 2009.

(51) Int. Cl.

| A61K 31/19 | (2006.01) |
| A61K 31/18 | (2006.01) |
| A61K 31/197 | (2006.01) |
| A61K 31/381 | (2006.01) |
| A61K 45/06 | (2006.01) |
| C07B 59/00 | (2006.01) |
| C07C 59/01 | (2006.01) |
| C07C 69/675 | (2006.01) |
| A61K 31/195 | (2006.01) |

(52) U.S. Cl.
CPC .............. *C07C 59/01* (2013.01); *A61K 31/19* (2013.01); *A61K 31/381* (2013.01); *A61K 45/06* (2013.01); *C07B 59/001* (2013.01); *C07C 69/675* (2013.01); *A61K 31/195* (2013.01); *C07B 2200/05* (2013.01)

(58) Field of Classification Search
CPC .... A61K 31/19; A61K 31/197; A61K 31/187; C07C 59/01
USPC .......................... 514/438, 557, 561; 562/579
See application file for complete search history.

(56) References Cited

U.S. PATENT DOCUMENTS

| 4,393,236 A | 7/1983 | Klosa |
| 4,548,716 A | 10/1985 | Boeve |
| 4,738,985 A | 4/1988 | Kluger et al. |
| 5,139,676 A | 8/1992 | Ebisawa et al. |
| 5,426,120 A | 6/1995 | Crepaldi et al. |
| 5,753,708 A | 5/1998 | Koehler et al. |
| 5,840,331 A | 11/1998 | Van Cauter et al. |
| 5,990,162 A | 11/1999 | Scharf |
| 6,204,245 B1 | 3/2001 | Siegel et al. |
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 7,727,549 B2 | 6/2010 | Kabra |
| 8,461,197 B2 | 6/2013 | Tung |
| 8,759,394 B2 | 6/2014 | Tung et al. |
| 9,051,261 B2 | 6/2015 | Tung |
| 9,309,182 B2 | 4/2016 | Tung et al. |
| 9,815,763 B2 | 11/2017 | Tung |
| 10,040,748 B2 | 8/2018 | Tung et al. |
| 10,532,971 B2 | 1/2020 | Tung |
| 11,161,798 B2 | 11/2021 | Tung |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0082380 A1 | 3/2009 | Czarnik |
| 2012/0122952 A1 | 5/2012 | Tung |
| 2015/0344398 A1 | 12/2015 | Tung |
| 2016/0326086 A1 | 11/2016 | Tung et al. |
| 2019/0100484 A1 | 4/2019 | Tung et al. |
| 2021/0403407 A1 | 12/2021 | Tung et al. |

FOREIGN PATENT DOCUMENTS

| EP | 1017381 B1 | 2/2005 |
| JP | S57-42651 A | 3/1982 |
| WO | 1992/19581 A1 | 11/1992 |
| WO | 1995/26325 A2 | 10/1995 |
| WO | 1998/41201 A1 | 9/1998 |
| WO | 2001/19361 A2 | 3/2001 |
| WO | 2002/24715 A2 | 3/2002 |
| WO | 2007/118651 A1 | 10/2007 |
| WO | 2010/42759 A2 | 4/2010 |
| WO | 2010/124046 A1 | 10/2010 |
| WO | 2012/112492 A1 | 8/2012 |

OTHER PUBLICATIONS

Baille, The use of stable isotopes in pharmacological research. Pharmacol Rev. Jun. 1981;33(2):81-132.
Blake et al., Studies with deuterated drugs. J Pharm Sci. Mar. 1975;64(3):367-91.

(Continued)

*Primary Examiner* — Raymond J Henley, III
(74) *Attorney, Agent, or Firm* — Paratus Law Group, PLLC

(57) ABSTRACT

This invention relates to novel derivatives of 4-hydroxybutyric acid and prodrugs thereof, and pharmaceutically acceptable salts of the foregoing. This invention also provides pharmaceutical compositions comprising a compound of this invention and the use of such compositions in methods of treating narcolepsy, fibromyalgia, other disorders or conditions that are beneficially treated by improving nocturnal sleep or by administering sodium oxybate.

11 Claims, No Drawings

(56) References Cited

OTHER PUBLICATIONS

Browne, Stable isotope techniques in early drug development: an economic evaluation. J Clin Pharmacol. Mar. 1998;38(3):213-20.
CAS Registry No. 1261393-42-3, Feb. 2, 2011.
CAS Registry No. 358730-90-2, Sep. 26, 2001.
Cherrah et al., Study of deuterium isotope effects on protein binding by gas chromatography/mass spectrometry. Caffeine and deuterated isotopomers. Biomed Environ Mass Spectrom. Nov. 1987;14(11):653-7.
Dyck et al., Effects of deuterium substitution on the catabolism of beta-phenylethylamine: an in vivo study. J Neurochem. Feb. 1986;46(2):399-404.
FDA Label, Xyrem—sodium oxybate solution. Jazz Pharmaceuticals, Inc., 18 pages, (2009).
Fisher et al., The complexities inherent in attempts to decrease drug clearance by blocking sites of CYP-mediated metabolism. Curr Opin Drug Discov Devel. Jan. 2006;9(1):101-9.
Foster, Deuterium Isotope Effects in Studies of Drug Metabolism. Trends in Pharmacological Sciences. Dec. 1984;5:524-527.
Foster, Deuterium Isotope Effects in the Metabolism of Drugs and Xenobiotics: Implications for Drug Design. Advances in Drug Research. 1985;14:1-40.
Friedrich et al., The Complete Stereochemistry of the Enzymatic Dehydration of 4-Hydroxybutyryl Coenzyme A to Crotonyl Coenzyme A. Angew Chem Int Ed. 2008;47:3524-3257.
Fukuto et al., Determination of the mechanism of demethylation of (methylenedioxy)phenyl compounds by cytochrome P450 using deuterium isotope effects. J Med Chem. Sep. 1991;34(9):2871-6.
Gouyette, Synthesis of deuterium-labelled elliptinium and its use in metabolic studies. Biomed Environ Mass Spectrom. Mar. 1, 1988;15(5):243-7.
Haskins, The application of stable isotopes in biomedical research. Biomed Mass Spectrom. Jul. 1982;9(7):269-77.
Honma et al., The metabolism of roxatidine acetate hydrochloride. Liberation of deuterium from the piperidine ring during hydroxylation. Drug Metab Dispos. Jul.-Aug. 1987;15(4):551-9.
Huisgen et al., Die Anlagerung Organischer Azide an Enoläther: Orientierung und Triazolin-Zerfall. Aus dem Institut für Organische Chemie Der Universität München. Oct. 9, 1964;98:1138-1152.
Kushner et al., Pharmacological uses and perspectives of heavy water and deuterated compounds. Can J Physiol Pharmacol. Feb. 1999;77(2):79-88.
Mamelak et al., Treatment of narcolepsy with gamma-hydroxybutyrate. A review of clinical and sleep laboratory findings. Sleep. 1986;9(1 Pt 2):285-9.
Peacock et al., Narcolepsy: clinical features, co-morbidities & treatment. Indian J Med Res. Feb. 2010;131:338-49.
Pearl et al., Succinic semialdehyde dehydrogenase deficiency: lessons from mice and men. J Inherit Metab Dis. Jun. 2009;32(3):343-52.
Pieniaszek et al., Moricizine bioavailability via simultaneous, dual, stable isotope administration: bioequivalence implications. J Clin Pharmacol. Aug. 1999;39(8):817-25.
Sabucedo et al., Extractionless GC/MS analysis of gamma-hydroxybutyrate and gamma-butyrolactone with trifluoroacetic anhydride and heptafluoro-1-butanol from aqueous samples. J Sep Sci. Jun. 2004;27(9):703-9.
Scharf et al., Pharmacokinetics of gammahydroxybutyrate (GHB) in narcoleptic patients. Sleep. Aug. 1, 1998;21(5):507-14.
STN Registry No. 591-81-1. Gamma-Hydroxybutyrate. Nov. 16, 1984. 1 page.
Struys et al., Metabolism of gamma-hydroxybutyrate to d-2-hydroxyglutarate in mammals: further evidence for d-2-hydroxyglutarate transhydrogenase. Metabolism. Mar. 2006;55(3):353-8.
Tonn et al., Simultaneous analysis of diphenhydramine and a stable isotope analog (2H10 diphenhydramine using capillary gas chromatography with mass selective detection in biological fluids from chronically instrumented pregnant ewes. Biol Mass Spectrom. Nov. 1993;22(11):633-42.
Tung, The Development of Deuterium-Containing Drugs. Innovations in Pharmaceutical Technology. Mar. 2010;32(32):24-28.
Wheatley et al., Use of deuterium labeling studies to determine the stereochemical outcome of palladium migrations during an asymmetric intermolecular Heck reaction. J Org Chem. Sep. 14, 2007;72(19):7253-9.
Wolen, The application of stable isotopes to studies of drug bioavailability and bioequivalence. J Clin Pharmacol. Jul.-Aug. 1986;26(6):419-24.
Zhang et al., Catabolism of 4-hydroxyacids and 4-hydroxynonenal via 4-hydroxy-4-phosphoacyl-CoAs. J Biol Chem. Nov. 27, 2009;284(48):33521-34.
International Search Report and Written Opinion for Application No. PCT/US2010/031981, dated Jul. 20, 2010, 3 pages.
International Search Report and Written Opinion for Application No. PCT/US2012/024974, dated May 4, 2012, 4 pages.

4-HYDROXYBUTYRIC ACID ANALOGS

CROSS-REFERENCE TO RELATED APPLICATIONS

This application is a continuation of U.S. application Ser. No. 16/739,422, filed Jan. 10, 2020, which is a continuation of U.S. application Ser. No. 15/810,526, filed Nov. 13, 2017 and now U.S. Pat. No. 10,532,971, which is a continuation of U.S. patent application Ser. No. 14/732,859, filed Jun. 8, 2015 and now U.S. Pat. No. 9,815,763, which is a continuation of U.S. patent application Ser. No. 13/914,127, filed Jun. 10, 2013 and now U.S. Pat. No. 9,051,261, which is a continuation of U.S. patent application Ser. No. 13/265,609, filed Feb. 2, 2012 and now U.S. Pat. No. 8,461,197. U.S. patent application Ser. No. 13/265,609 is a U.S. national stage filing, under 35 U.S.C. § 371(c), of International Application PCT/US2010/031981, filed Apr. 22, 2010, which claims the benefit of U.S. Application No. 61/214,382, filed Apr. 23, 2009 and U.S. Application No. 61/287,561, filed Dec. 17, 2009. The entire teachings of each of the aforementioned applications are incorporated herein by reference.

BACKGROUND OF THE INVENTION

4-Hydroxybutyric acid is a well-known hypnotic agent. Though its mechanism of action is poorly understood, 4-hydroxybutyrate has been characterized as inhibiting polysynaptic reflexes while retaining monosynaptic reflexes. It typically induces sleep while maintaining good respiration (Basil, B. et al., Br J Pharmacol Chemother, 1964, 22:318 and increases delta sleep (stage 3 and stage 4) while decreasing light or stage 1 sleep (Scrima, L. et al., Sleep, 1990, 13:479; Pardi, D. and Black, J., CNS Drugs, 2006, 20:993.

The sodium salt of 4-hydroxybutyric acid, known generically as sodium oxybate and marketed as Xyrem®, is approved for the treatment of excessive daytime sleepiness and cataplexy in patients with narcolepsy. It is effective for relieving pain and improving function in patients with fibromyalgia syndrome (Scharf, M B et al., J Rheumatol, 2003, 30:1070; Russell, I J et al., Arthritis Rheum 2009, 60:299). Sodium oxybate has also been reported to be effective in alleviating excessive daytime sleepiness and fatigue in patients with Parkinson's disease, improving myoclonus and essential tremor, and reducing tardive dyskinesia and bipolar disorder (Ondo, W G et al., Arch Neurol, 2008, 65:1337; Frucht, S J et al, Neurology, 2005, 65:1967; Berner, J E, J Clin Psychiatry, 2008, 69:862).

Despite a general record of safety when used as prescribed, impaired respiration has been reported in some patients following a typical dose of sodium oxybate (see, e.g., FDA product label dated Nov. 13, 2006 for NDA no. 021196). Headache, nausea, and dizziness were observed in clinical trials at rates of 17-22%. These adverse effects were dose-dependent.

The use of 4-hydroxybutyric acid can be inconvenient because of its very short half life in humans (0.5-1 hour). Many patients report needing to take two separate doses of the drug during the night to maintain sleep. Consequently, despite the desirable and beneficial effects of 4-hydroxybutyric acid, there is a continuing need for new compounds to treat the aforementioned diseases and conditions.

SUMMARY OF THE INVENTION

This invention relates to novel derivatives of 4-hydroxybutyric acid and prodrugs thereof, and pharmaceutically acceptable salts of the foregoing. This invention also provides pharmaceutical compositions comprising a compound of this invention and the use of such compositions in methods of selectively inhibiting polysynaptic reflexes without significantly affecting monosynaptic reflexes, and treating narcolepsy, fibromyalgia, other disorders and conditions that are beneficially treated by improving nocturnal sleep or by administering sodium oxybate.

DETAILED DESCRIPTION

The term "treat" as used herein means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of sodium oxybate will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. Unless otherwise indicated, "stereoisomer" refers to both enantiomers and diastereomers.

The term "optionally substituted with deuterium" means that one or more hydrogen atoms in the referenced moiety may be replaced with a corresponding number of deuterium atoms.

The term "$C_{2-10}$ alkoxyalkyl" refers to a moiety of the formula —$(CH_2)_a$—O—$(CH_2)_b$, wherein each of a and b is an integer between 1 and 9; and the sum of a+b is an integer between 2 and 10.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula B:

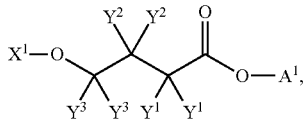

or a pharmaceutically acceptable salt thereof, wherein:
$A^1$ is hydrogen, deuterium, —$CH_2$—C(O)$OR^{2'}$ or —CH($R^{1'}$)—C(O)$OR^{2'}$;
$R^{1'}$ is $C_{1-6}$alkyl, $C_{2-10}$alkoxyalkyl, phenyl, —($C_{1-3}$alkyl)-($C_{3-6}$cycloalkyl), or $C_{3-6}$ cycloalkyl, wherein $R^{1'}$ is optionally substituted with $C_{1-3}$alkyl, $C_{1-3}$alkoxy, phenyl, or —O—($CH_2CH_2O)_n$—$CH_3$, wherein n is 1, 2, or 3;
$R^{2'}$ is hydrogen; deuterium; —$C_{1-4}$alkyl optionally substituted with phenyl; —($C_{3-6}$cycloalkyl) optionally substituted with phenyl or methyl; —$CH_2$—($C_{3-6}$cycloalkyl) wherein the $C_{3-6}$cycloalkyl is optionally substituted with phenyl; phenyl; or biphenyl;
$X^1$ is hydrogen, deuterium, —C(O)-indanyl, —C(O)-indenyl, —C(O)-tetrahydronaphthyl, —C(O)—$C_{1-6}$alkyl, —C(O)—$C_{1-6}$alkenyl, —C(O)—$C_{1-6}$alkynyl, —C(O)—$C_{1-3}$alkyl optionally substituted with $C_{3-6}$cycloalkyl, or —C(O)—$C_{3-6}$cycloalkyl optionally substituted with $C_{1-6}$ alkyl, phenyl or naphthyl; and
each Y is independently selected from hydrogen and deuterium, provided that:
(i) when $A^1$ is hydrogen or deuterium, at least one Y is deuterium; and
(ii) when $X^1$ is hydrogen or deuterium, each $Y^2$ is deuterium, and each $Y^3$ is deuterium, then $A^1$ is not hydrogen or deuterium.

In one embodiment of Formula B, at least one Y is deuterium. In one aspect of this embodiment, $X^1$ is not hydrogen or deuterium.

In one embodiment of Formula B, $R^{2'}$ is hydrogen, —$C_{1-4}$ alkyl, —$C_{3-6}$cycloalkyl, —$CH_2$—($C_{3-6}$cycloalkyl), phenyl or benzyl, and at least one Y is deuterium.

In a more specific embodiment of a compound of Formula B, $A^1$ is —$CH_2$—C(O)$OR^{2'}$ or —CH($R^{1'}$)—C(O)$OR^{2'}$; $R^{1'}$ is $C_{1-4}$alkyl; each $Y^1$ is the same; each $Y^2$ is the same; each $Y^3$ is hydrogen; $X^1$ is hydrogen, —C(O)$CH_3$, or —C(O)$CH_2$Ph, provided that at least one of $Y^1$ and $Y^2$ is deuterium. In one aspect of this embodiment, $R^{2'}$ is —$CH_3$, —$CH_2CH_3$, or benzyl.

In another embodiment of Formula B: $A^1$ is hydrogen; each $Y^1$ is the same; each $Y^2$ is the same; each $Y^3$ is hydrogen; and $X^1$ is selected from acetyl and benzoyl, provided that at least one of $Y^1$ and $Y^2$ is deuterium. In one aspect of this embodiment, each $Y^1$ is deuterium.

In one embodiment of Formula B, $A^1$ is —CH($R^{1'}$)—C(O)$OR^{2'}$, the compound having the structure of Formula B-II:

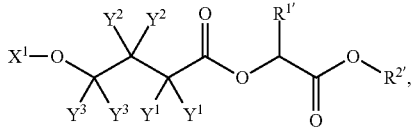

or a pharmaceutically acceptable salt thereof, wherein $X^1$, Y, $R^{1'}$ and $R^{2'}$ are as described above for Formula B.

In compounds of Formula B-II, the carbon atom bearing $R^{1'}$ has a chiral center. In one embodiment, the compound of Formula B-II has the (S) configuration at that chiral center as shown in Formula (S)-B-II below.

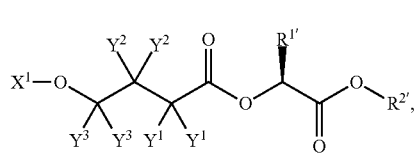

In certain embodiments of compounds of Formula B, B-II and (S)-B-II, each $Y^1$ is the same; each $Y^2$ is the same; and each $Y^3$ is the same, and at least one pair of Y (e.g., each $Y^1$; each $Y^2$; or each $Y^3$) is deuterium. In one specific aspect, each $Y^3$ is hydrogen.

Another embodiment of Formula B provides a compound wherein each $Y^3$ is hydrogen and $A^1$ is —$CH_2$—C(O)$OR^{2'}$, the compound having the structure shown in Formula B-III:

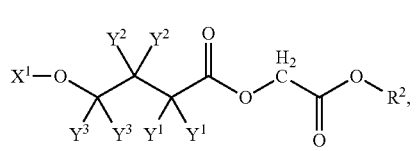

or a pharmaceutically acceptable salt thereof, wherein the $X^1$, Y and $R^{2'}$ variables are as described above for Formula B.

In certain embodiments of compounds of Formula B-III, each $Y^1$ is the same; each $Y^2$ is the same; and each $Y^3$ is the same, and at least one pair of Y (e.g., each $Y^1$; each $Y^2$; or each $Y^3$) is deuterium. In one specific aspect, each $Y^3$ is hydrogen.

The present invention also provides a compound of Formula I:

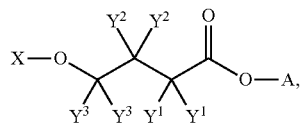

or a pharmaceutically acceptable salt thereof, wherein:
A is hydrogen, deuterium, —$CH_2$—CH(O)$OR^2$ or —CH($R^1$)—C(O)$OR^2$;
$R^1$ is a $C_{1-6}$alkyl, $C_{2-10}$alkoxyalkyl, or $C_{3-6}$cycloalkyl group that is optionally substituted by an $R^3$ group;
$R^3$ is $C_{1-3}$alkyl, $C_{1-3}$alkoxy, phenyl, —O—($CH_2CH_2O)_n$—$CH_3$, or -(heterocyclyl)-$C_{1-3}$alkyl where the heterocyclyl moiety is a four to six-membered ring having an oxygen ring atom;
n is 1, 2, or 3;
$R^2$ is hydrogen, deuterium, —$C_{1-4}$alkyl, —$C_{1-4}$alkyl-phenyl, —$C_{3-6}$ cycloalkyl, —$C_{3-6}$cycloalkyl-phenyl, —$CH_2$—($C_{3-6}$cycloalkyl), —$CH_2$—($C_{3-6}$cycloalkyl)-phenyl, phenyl, or biphenyl;
X is hydrogen, deuterium, —C(O)-indanyl, —C(O)-indenyl, —C(O)-tetrahydronaphthyl, —C(O)—$C_{1-6}$ alkyl, —C(O)—C$_{1-6}$ alkenyl, —C(O)—C$_{1-6}$alkynyl, —C(O)—C$_{1-3}$alkyl-(C$_{3-6}$ cycloalkyl), or —C(O)—C$_{3-6}$ cycloalkyl optionally substituted by C$_{1-6}$alkyl, phenyl or naphthyl; and each Y is independently selected from hydrogen and deuterium, provided that when A is hydrogen at least one Y is deuterium.

In one embodiment of Formula I, each Y is independently selected from hydrogen and deuterium, provided that when A is hydrogen at least one Y is deuterium and X is not hydrogen.

Examples of the R$^3$ heterocyclyl moiety of Formula I include oxetane, tetrahydrofuran, furan, tetrahydropyran and pyran.

In one embodiment of Formula I, R$^2$ is hydrogen, —C$_{1-4}$ alkyl, —C$_{3-6}$cycloalkyl, —CH$_2$—(C$_{3-6}$cycloalkyl), phenyl or benzyl.

In a more specific embodiment of a compound of Formula I A is —CH$_2$—C(O)OR$^2$ or —CH(R$^1$)—C(O)OR$^2$; R$^1$ is C$_{1-4}$ alkyl; each Y$^1$ is the same; each Y$^2$ is the same; each Y$^3$ is hydrogen; X is hydrogen, —C(O)CH$_3$, or —C(O)CH$_2$Ph. In one aspect of this embodiment, R$^2$ is —CH$_3$, —CH$_2$CH$_3$, or benzyl.

In another embodiment of Formula I: A is hydrogen; each Y$^1$ is the same; each Y$^2$ is the same; each Y$^3$ is hydrogen; and X is selected from acetyl and benzoyl. In one aspect of this embodiment, each Y$^1$ is deuterium.

In one embodiment of Formula I, A is —CH(R$^1$)—C(O)OR$^2$, the compound having the structure of Formula II:

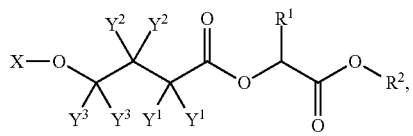

II or a pharmaceutically acceptable salt thereof, wherein X, Y, R$^1$ and R$^2$ are as described above for Formula I.

In compounds of Formula II, the carbon atom bearing R$^1$ has a chiral center. In one embodiment, the compound of Formula II has the (S) configuration at that chiral center as shown in Formula (S)-II below.

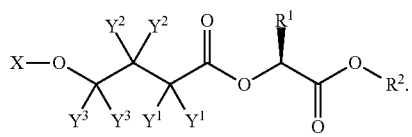

(S)-II

In certain embodiments of compounds of Formula I, II and S-II, each Y$^1$ is the same; each Y$^2$ is the same; and each Y$^3$ is the same. In one specific aspect, each Y$^3$ is hydrogen.

Another embodiment of Formula II provides a compound wherein each Y$^3$ is hydrogen and R$^1$ is hydrogen, the compound having the structure shown in Formula III:

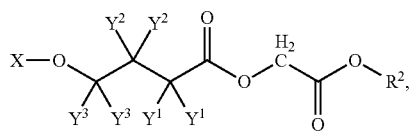

III or a pharmaceutically acceptable salt thereof, wherein the X, Y and R$^2$ variables are as described above for Formula I.

Table 1 shows examples of specific compounds of Formula III.

TABLE 1

Examples of Specific Compounds of Formula III

| Compound # | X | Each Y$^1$ | Each Y$^2$ | R$^2$ |
|---|---|---|---|---|
| 100 | H | H | H | CH$_3$ |
| 101 | H | H | H | C$_2$H$_5$ |
| 102 | H | H | H | CH$_2$C$_6$H$_5$ |
| 103 | H | D | H | CH$_3$ |
| 104 | H | D | H | C$_2$H$_5$ |
| 105 | H | D | H | CH$_2$C$_6$H$_5$ |
| 106 | H | H | D | CH$_3$ |
| 107 | H | H | D | C$_2$H$_5$ |
| 108 | H | H | D | CH$_2$C$_6$H$_5$ |
| 109 | Ac | H | H | CH$_3$ |
| 110 | Ac | H | H | C$_2$H$_5$ |
| 111 | Ac | H | H | CH$_2$C$_6$H$_5$ |
| 112 | Ac | D | H | CH$_3$ |
| 113 | Ac | D | H | C$_2$H$_5$ |
| 114 | Ac | D | H | CH$_2$C$_6$H$_5$ |
| 115 | Ac | H | D | CH$_3$ |
| 116 | Ac | H | D | C$_2$H$_5$ |
| 117 | Ac | H | D | CH$_2$C$_6$H$_5$ |
| 118 | H | H | H | H |

In certain embodiments, the compound of Formula III is a pharmaceutically acceptable salt of any one of the compounds set forth in Table 1.

In another embodiment the invention provides a compound selected from any one of

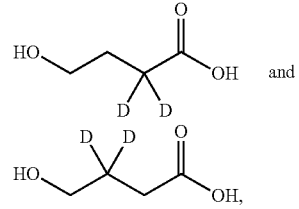

and or a pharmaceutically acceptable salt thereof.

In another embodiment the invention provides the compound

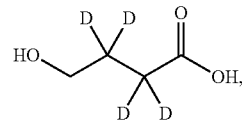

or a pharmaceutically acceptable salt thereof.

In yet another embodiment, the invention provides a compound selected from any one of HO—CH$_2$—CH$_2$—CD$_2$-C(O)—O$^-$ Na$^+$, HO—CH$_2$—CD$_2$-CD$_2$-C(O)O$^-$ Na$^+$, and HO—CH$_2$—CD$_2$-CH$_2$—C(O)—O$^-$ Na$^+$.

In another set of embodiments, any atom not designated as deuterium in any of the embodiments set forth above is present at its natural isotopic abundance.

In one embodiment the invention provides any one of the following compounds, where any atom not designated as deuterium is present in its natural abundance:

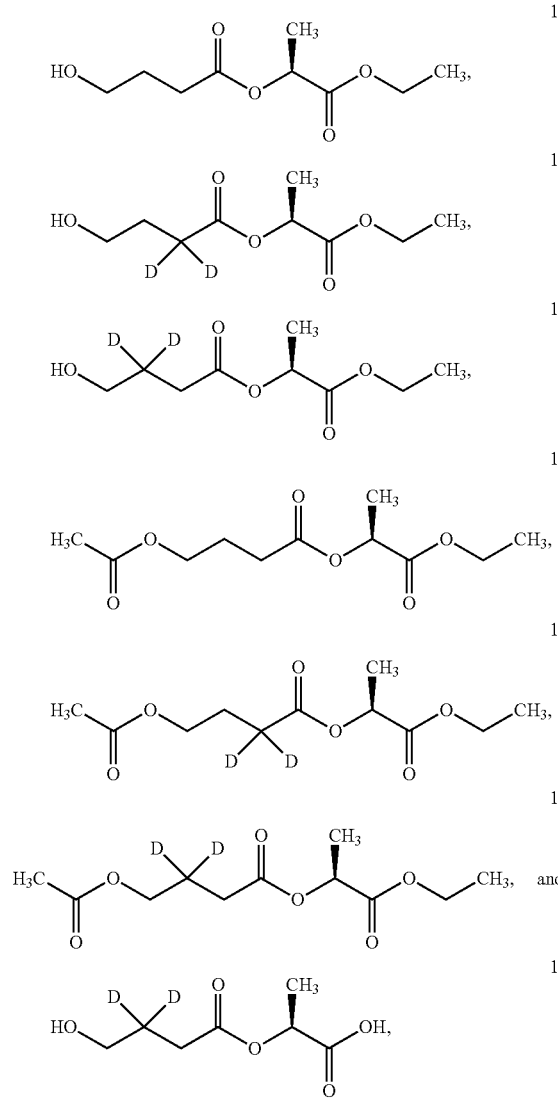

or a pharmaceutically acceptable salt of any of the foregoing.

The synthesis of compounds of Formula I can be readily achieved by synthetic chemists of ordinary skill. Relevant procedures and intermediates such as methyl, ethyl, and benzyl lactate esters, as well as acetic anhydride and benzoic anhydride are commercially available. Methods for esterifying alcohols are described in Greene T W et al., *Protective Groups in Organic Synthesis,* 3rd Ed., John Wiley and Sons (1999).

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Scheme 1.

Compounds of this invention can readily be made by means known in the art of organic synthesis.

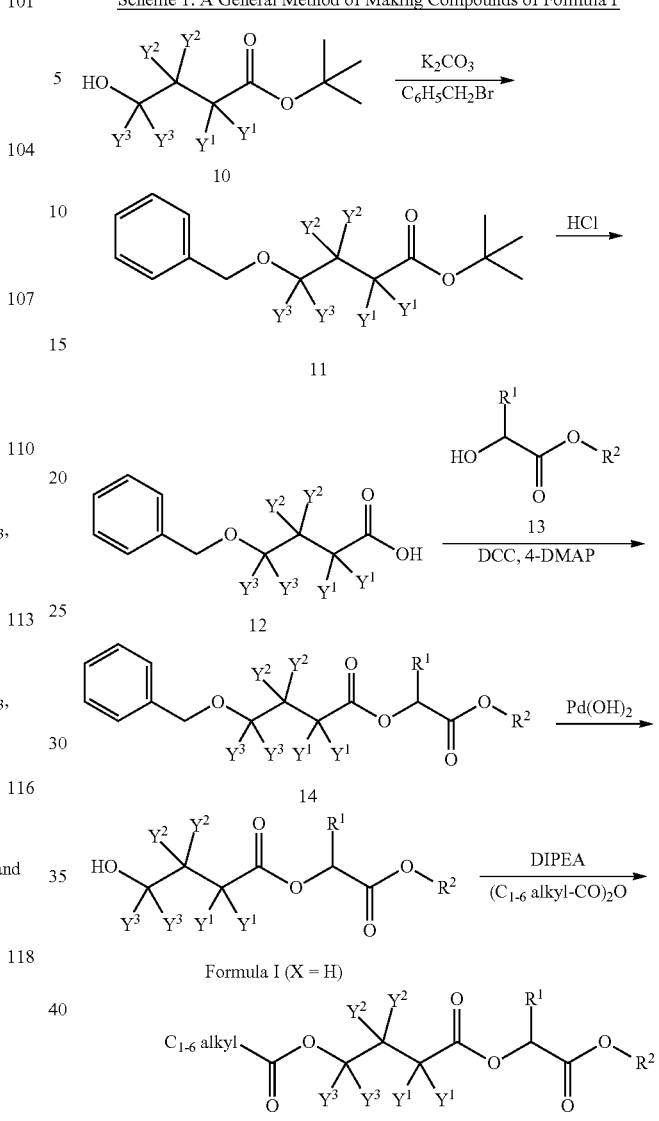

Scheme 1 shows a general method for making compounds of Formula I. Alkylation of the alcohol group of an appropriately deuterated tert-butyl ester of 4-hydroxybutyric acid 10 is achieved by means known in the art, for instance by using benzyl bromide as an alkylating agent with potassium carbonate as a base in an aprotic solvent to produce the benzyl ester 11. Acidolytic removal of the tert-butyl group, for instance by using excess anhydrous hydrogen chloride dissolved in an inert solvent, produces the corresponding acid 12. Esterification of the resulting acid 12 with an appropriate ester 13 using dicyclohexylcarbodiimide ("DCC") with catalytic 4-dimethylaminepyridine ("4-DMAP") produces the corresponding diester 14. The benzyl group is then removed by catalytic hydrogenation using palladium hydroxide as the catalyst to produce a compound of Formula I, wherein X is hydrogen. Acetylation of this compound of Formula I using an anhydride and a tertiary amine base such as diisopropylethylamine ("DIPEA") produces a compound of Formula I, where X is —C(O)—$C_1$-$C_6$alkyl.

Scheme 2. Synthesis of a Deuterated Tert-butyl Ester of 4-hydroxybutyric acid wherein each Y¹ is deuterism (10-2,2-d2)

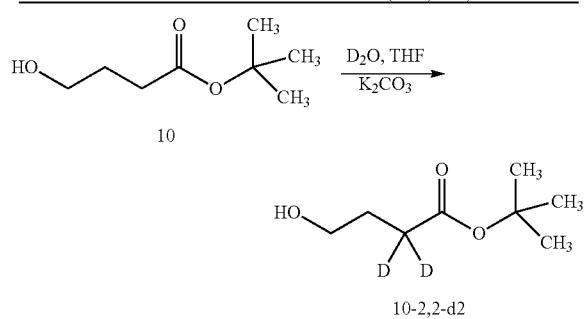

Scheme 2 shows a method for the regioselective deuteration of the 2 position of commercially available 4-hydroxybutyric acid tert-butyl ester (10) to yield the 2,2-dideutero species (10-d2). Reaction with a deuterium donor such as $D_2O$, optionally using a co-solvent such as THF, and a base such $K_2CO_3$ provides 4-hydroxybutyrate compounds where each Y¹ is deuterium. In order to obtain the desired level of deuterium substitution, several such exchange reactions may be carried out in sequence. Such a sequence may provide deuterium incorporation of at least 90% and typically greater than 95% at each Y¹ position. The resulting selectively deuterated compound can then be carried through the reaction sequence specified in Scheme 1 to produce compounds of Formula I, wherein each Y¹ is deuterium.

Scheme 3. Synthesis of a Deuterated Tert-butyl Ester of 4-hydroxybutric acid wherein each Y² is deuterium (10-3,3-d2)

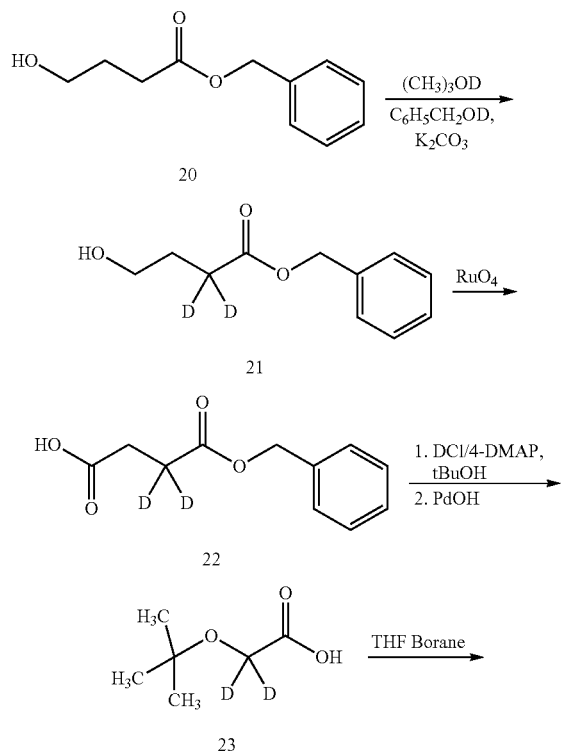

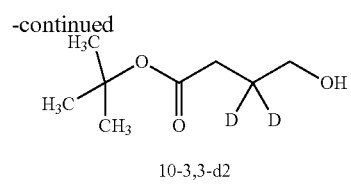

10-3,3-d2

Scheme 3 shows a method for selective deuterium substitution at the 3-position (Y²). Deuterium substitution of commercially available benzyl 4-hydroxybutyrate (20), using $(CH_3)_3OD$ and a small amount of $C_6H_5CH_2OD$ as deuterium donors, and a base such as $K_2CO_3$, produces the 2,2-dideutero alcohol species 21. The oxidation of the alcohol 21 using ruthenium tetroxide under neutral conditions produces the carboxylic acid 22. Tert-butyl esterification of the carboxylic acid 22 using DCC with a catalytic amount of 4-dimethylaminepyridine and tert-butyl alcohol is followed by cleavage of the benzyl ester by catalytic hydrogenation using palladium hydroxide to produce the t-butoxy carboxylic acid 23. Selective reduction of the carboxylic acid 23 using borane in THF complex produces 3,3-dideutero-4-hydroxybutyric acid tert-butyl ester (10-3,3-d2), which can be used in Scheme 1 to produce compound of Formula I, wherein Y³ is deuterium.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R¹, R², R³, etc.) or not. The suitability of a chemical group in a compound structure for use in the synthesis of another compound is within the knowledge of one of ordinary skill in the art.

Analogous methods to the ones shown in Schemes 1-3 for compounds of Formula I may be used for synthesizing compounds of Formula B as.

Additional methods of synthesizing compounds of Formula I or Formula B and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free pharmaceutical compositions comprising an effective amount of a compound of Formula I (e.g., including any of the compounds of formulae II, (S)-II, or III herein) or Formula B, B-II, (S)-B-II or B-III, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and U.S. patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, PA (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, if a protic solvent such as water or alcohols is used to dissolve or suspend a compound of this invention in a pharmaceutical composition, the solvent is preferably deuterated (e.g. $D_2O$, $CH_3CH_2OD$, $CH_3CH_2OD$). In these cases the proton on the hydroxy groups of the compound of Formula I or B will be partially or mostly replaced with deuterium. Compounds of Formula I or B comprising a deuterated hydroxy group in place of —OH are also part of the present invention.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with sodium oxybate.

In one embodiment, the second therapeutic agent is useful in the treatment of abnormal nocturnal sleep, and conditions beneficially treated by improving nocturnal sleep, such as narcolepsy, and fibromyalgia. In another embodiment, the second therapeutic agent is useful in selectively inhibiting polysynaptic reflexes in a patient without significantly affecting monosynaptic reflexes.

In another embodiment, the second therapeutic agent is selected from dual serotonin-norepinephrine reuptake inhibitors and alpha2-delta subunit calcium channel modulators.

Examples of dual serotonin-norepinephrine reuptake include, but are not limited to, duloxetine, milnacipran, and venlafaxine.

Examples of alpha2-delta subunit calcium channel modulators include, but are not limited to, pregabalin, gabapentin, and prodrugs thereof.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.05-2.5 mmol of a compound of Formula I Formula I or pharmaceutically acceptable salt thereof/kg of body weight, preferably between about 0.15-1.5 mmol/kg. When treating a human patient in need of improved nocturnal sleep, the selected dose is preferably administered orally from 1-2 times daily. More preferably the selected dose is administered orally 1 time daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for sodium oxybate.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

According to another embodiment, the invention provides a method of treating a disease or condition that is beneficially treated by a sodium oxybate in a patient in need thereof, comprising the step of administering to the patient an effective amount of a compound or a composition of this invention. Such diseases and conditions include, but are not limited to, abnormal nocturnal sleep, and conditions beneficially treated by improving nocturnal sleep, such as narcolepsy, and fibromyalgia. In another embodiment, the method is used to selectively inhibit polysynaptic reflexes in a patient without significantly affecting monosynaptic reflexes.

In one particular embodiment, the method of this invention is used to improve nocturnal sleep in a patient in need thereof.

Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient in need thereof one or more second therapeutic agents. The choice of second therapeutic agent may be made from any second therapeutic agent known to be useful for co-administration with sodium oxybate. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or Formula B or pharmaceutically acceptable salt thereof and a second therapeutic agent to a patient in need thereof selected from dual serotonin-norepinephrine reuptake inhibitors and alpha2-delta subunit calcium channel modulators.

In one embodiment, the second therapeutic agent is a dual serotonin-norepinephrine reuptake selected from duloxetine, milnacipran, and venlafaxine.

In another embodiment, the second therapeutic agent is an alpha2-delta subunit calcium channel modulators selected from pregabalin, gabapentin, and prodrugs thereof.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I Formula I or pharmaceutically acceptable salt thereof alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I or pharmaceutically acceptable salt thereof for use in the treatment or prevention in a patient of a disease, disorder or symptom thereof delineated herein.

Pharmaceutical Kits

The present invention also provides kits for use in improving nocturnal sleep These kits comprise (a) a pharmaceutical composition comprising a compound of Formula I or Formula B, or a pharmaceutically acceptable salt thereof, wherein said pharmaceutical composition is in a container; and (b) instructions describing a method of using the pharmaceutical composition to improve nocturnal sleep.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1. Sodium 2,2-d2-4-hydroxybutyrate

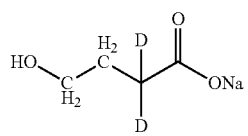

Sodium 2,2-d2-4-hydroxybutyrate is prepared in the following manner: treatment of succinic anhydride with tert-butanol, N-hydroxysuccinimide, and 4-dimethylaminopyridine (4-DMAP) according to the procedure of Yao, Z-J., et al, J. Org. Chem. 2003, 68, 6679-6684 affords the succinic acid mono-tert-butyl ester. In accordance with Yao, reduction of the succinic acid with borane-dimethyl sulfide complex gives the 4-hydroxybutanoic acid tert-butyl ester. Subjecting the ester to hydrogen/deuterium exchange by treatment with potassium carbonate in d1-methanol affords the 2,2-d2-4-hydroxybutanoic acid tert-butyl ester. Finally, saponification of the tert-butyl ester with sodium hydroxide in d1-methanol in a manner analogous to the procedure of Goto, G., et al, Chem. Pharm. Bull. 1985, 33, 4422-4431 affords the desired sodium 2,2-d2-4-hydroxybutyrate.

Example 2. Sodium 3,3-d2-4-hydroxybutyrate

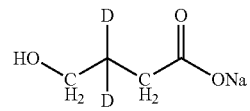

Sodium 3,3-d2-4-hydroxybutyrate is prepared in the following manner: treatment of mono-methylsuccinate with sodium methoxide in d1-methanol in a manner analogous to the procedure of Keay, B. A., et al., J. Org. Chem. 2007, 72, 7253-7259 affords the butanedioic-2,2-d2 acid, 1-methyl ester. Treatment of the d2 ester in a manner analogous to Keay et al. with sodium borohydride in water affords the 4,4-dideutero-dihydrofuran-2(3H)-one. Finally, saponification of the dideutro-butyrolactone with sodium hydroxide in d1-methanol in a manner analogous to the procedure of Goto, G., et al, Chem. Pharm. Bull. 1985, 33, 4422-4431 affords the desired sodium 3,3-d2-4-hydroxybutyrate.

Example 3. Sodium 2,2,3,3-d4-4-hydroxybutyrate

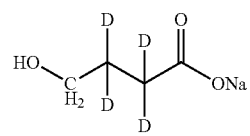

Sodium 2,2,3,3-d4-4-hydroxybutyrate is prepared in the following manner: treatment of 3,3,4,4-d4-tetrahydrofuran with calcium hypochlorite in acetonitrile according to the procedure of de Meijere, A. et al., Chem. Eur. J. 2007, 13, 167-177 affords the 3,3,4,4-tetradeutero-dihydrofuran-2 (3H)-one. Saponification of the tetradeutero-butyrolactone with sodium hydroxide in d1-methanol in a manner analogous to the procedure of Goto, G., et al, Chem. Pharm. Bull. 1985, 33, 4422-4431 affords the desired sodium 2,2,3,3-d4-4-hydroxybutyrate.

The above-identified deuterated 4-hydroxybutyrate sodium salts are converted to their corresponding esters by treatment with the corresponding alkyl halide in the presence of an aqueous base in a manner analogous to the procedure of U.S. Pat. No. 5,250,696.

Example 4. Evaluation of Metabolic Stability in Human Liver Microsomes

Human liver microsomes (20 mg/mL) are obtained from Xenotech, LLC (Lenexa, KS). β-nicotinamide adenine dinucleotide phosphate, reduced form (NADPH), magnesium chloride (MgCl$_2$), and dimethyl sulfoxide (DMSO) are purchased from Sigma-Aldrich.

Determination of Metabolic Stability: 7.5 mM stock solutions of test compounds are prepared in DMSO. The 7.5 mM stock solutions are diluted to 12.5 µM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes (375 µL) are added to wells of a 96-well deep-well polypropylene plate in triplicate. 10 µL of the 12.5 µM test compound is added to the microsomes and the mixture is pre-warmed for 10 minutes. Reactions are initiated by addition of 125 µL of pre-warmed NADPH solution. The final reaction volume is 0.5 mL and contains 0.5 mg/mL human liver microsomes, 0.25 µM test compound, and 2 mM NADPH in 0.1 M potassium phosphate buffer, pH 7.4, and 3 mM MgCl$_2$. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent compound remaining by LC-MS/MS using an Applied Biosystems API 4000 mass spectrometer. 7-ethoxycoumarin (1 µM) is used as the positive control substrate.

Data analysis: The in vitro half-lives ($t_{1/2}$s) for test compounds are calculated from the slopes of the linear regression of % parent remaining (ln) vs incubation time relationship using the following formula:

$$\text{in vitro } t_{1/2} = 0.693/k,$$
$$\text{where } k = -\frac{[\text{slope of linear regression of \% parent remaining(ln) } vs \text{ incubation time}]}{}$$

Data analysis is performed using Microsoft Excel Software.

The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of the Formula B:

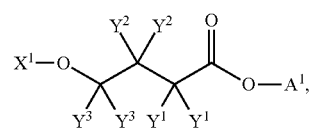

or a pharmaceutically acceptable salt thereof, wherein:
A$^1$ is —CH$_2$—C(O)OR$^{2'}$;
R$^{2'}$ is hydrogen; deuterium; —C$_{1-4}$ alkyl optionally substituted with phenyl; —(C$_{3-6}$ cycloalkyl) optionally substituted with phenyl or methyl; —CH$_2$—(C$_{3-6}$ cycloalkyl) wherein the C$_{3-6}$ cycloalkyl is optionally substituted with phenyl; phenyl; or biphenyl;
X$^1$ is hydrogen;
each Y is independently selected from hydrogen and deuterium, wherein at least one Y is deuterium; and
wherein each position designated as deuterium has a deuterium incorporation of at least 90%.

2. The compound of claim 1, wherein:
R$^{2'}$ is hydrogen, —C$_{1-4}$ alkyl, —C$_{3-6}$ cycloalkyl, —CH$_2$—(C$_{3-6}$ cycloalkyl), phenyl or benzyl.

3. The compound of claim 1, wherein at least one pair of Y are deuterium.

4. The compound of claim 1, wherein any atom not designated as deuterium in any of the embodiments set forth above is present at its natural isotopic abundance.

5. A pharmaceutical composition comprising a compound of claim 1 or a pharmaceutically acceptable salt thereof; and a pharmaceutically acceptable carrier.

6. The pharmaceutical composition of claim 5, additionally comprising a second therapeutic agent selected from a dual serotonin-norepinephrine reuptake inhibitor and an alpha2-delta subunit calcium channel modulator.

7. The pharmaceutical composition of claim 6, wherein the second therapeutic agent is selected from duloxetine, milnacipran, venlafaxine, pregabalin, gabapentin, and prodrugs thereof.

8. A method of treating a disease or disorder selected from abnormal nocturnal sleep, narcolepsy, fibromyalgia, other diseases or disorders beneficially treated by improving nocturnal sleep or by administering sodium oxybate comprising the step of administering to a patient in need thereof an effective amount of a composition of claim 5.

9. The method of claim 8, comprising the additional step of co-administering to the patient in need thereof a second therapeutic agent selected from a dual serotonin-norepinephrine reuptake inhibitor and an alpha2-delta subunit calcium channel modulator.

10. The method of claim 9, wherein the second therapeutic agent is selected from duloxetine, milnacipran, venlafaxine, pregabalin, gabapentin, and prodrugs thereof.

11. A method of selectively inhibiting polysynaptic reflexes without significantly affecting monosynaptic reflexes in a patient in need thereof comprising the step of administering to the patient an effective amount of a composition of claim 5.

* * * * *